US005219995A

United States Patent [19]

Herring et al.

[11] Patent Number: 5,219,995
[45] Date of Patent: Jun. 15, 1993

[54] PLASMA FRACTION PURIFICATION

[75] Inventors: Steven W. Herring, San Dimas; Yahiro Uemura, Arcadia, both of Calif.; Munehiro Noda, Nara, Japan; Kenneth T. Shitanishi, North Hollywood, Calif.

[73] Assignee: Alpha Therapeutic Corporation, Los Angeles, Calif.

[21] Appl. No.: 913,590

[22] Filed: Jul. 14, 1992

[51] Int. Cl.$^5$ .................. C07K 15/06; C07K 3/20; C07K 3/24
[52] U.S. Cl. .................. 530/381; 530/384; 530/413; 530/416; 530/417; 530/420
[58] Field of Search .............. 530/384, 381, 416, 420, 530/413, 417; 514/12, 21

[56] References Cited

U.S. PATENT DOCUMENTS 4,725,673  2/1988  Herring .................. 530/381

OTHER PUBLICATIONS

Fasco et al., "Human α-, β(T)-, γ(T)-Thrombins," Div. Lab. and Res., New York State Dept. of Health, Albany, N.Y. 12201 (Abstract) *Physiology*, 765.
Mannis et al., "Uses of Thrombin in Ocular Surgery: Effect on the Corneal Endothelium," *Arch. Ophthalmol.*, 106, 251–253 (1988).
Krishnaswamy et al., "Activation of Human Prothrombin by Human Prothrombinase: Influence of Factor Va on the Reaction Mechanism," *J. Biol. Chem.*, 262, 3291–3299 (1987).
Helmkamp et al., "Effectiveness of topical hemostatic agents," *Contemporary OB/GYN*, 171–180 (1985).
Ghosh et al., "Note on the Preparation of Bovine Thrombin," *Thrombosis Research*, 20, 281–283 (1980).
Pepper et al., "Chromatography of Human Prothrombin Complex on Dextran Sulphate Agarose," *Thrombosis Research*, II, 687–692 (1977).
Fenton et al., "Human Thrombins: Production, Evaluation, and Properties of α-Thrombin," *J. Biol. Chem.*, 252, 3587–3598 (1977).
Lundblad, Roger L., "A Rapid Method for the Purification of Bovine Thrombin and the Inhibition of the Purified Enzyme with Phenylmethylsulfonyl Fluoride," *Biochem.*, 10, 2501–2506 (1972).
Denson et al., "The Specific Assay of Prothrombin Using the Taipan Snake Venom," *Brit. J. Haematol.*, 21, 219–226 (1971).
Seegers et al., "Preparation and Properties of Thrombin," *Arch. Biochem. & Biophys.*, 128, 194–201 (1968).
Seegers et al., "Purification of Prothrombin and Thrombin by Chromatography on Cellulose," *Can. J. Biochem. Physiol.*, 38, 1405–1410 (1960).
Tidrick et al., "Clinical Experience with Thrombin as an Hemostatic Agent," *Surgery*, 14, 191–196 (1943).

*Primary Examiner*—Jeffrey E. Russel
*Assistant Examiner*—P. Lynn Touzeau
*Attorney, Agent, or Firm*—Christie, Parker & Hale

[57] ABSTRACT

The present invention describes a process for activating Factor II to Factor II$_a$ by incubating Factor II in the presence of Factor V, Factor X$_a$, phospholipids, and calcium ions. Each of the factors is prepared from a single impure protein fraction which includes Factors II, V and X. The Factor II, V and X purification procedure comprises the steps of DEAE ligand chromatography and precipitation by the addition of barium chloride. Factor V is recovered from the barium chloride supernatant, and Factors II and X are contained in the barium chloride precipitate. The barium chloride precipitate is dissolved in an aqueous solution and is applied to a chromatographic resin coupled with a ligand which binds Factor X and Factor II weakly or not at all. Factor II is recovered from the fraction, which remains unbound or weakly bound to the Factor X binding ligand. Factor X$_a$ is prepared by recovering Factor X from the ligand during the Factor II preparation procedure and activating the Factor X to Factor X$_a$ by specific proteolytic cleavage.

26 Claims, 1 Drawing Sheet

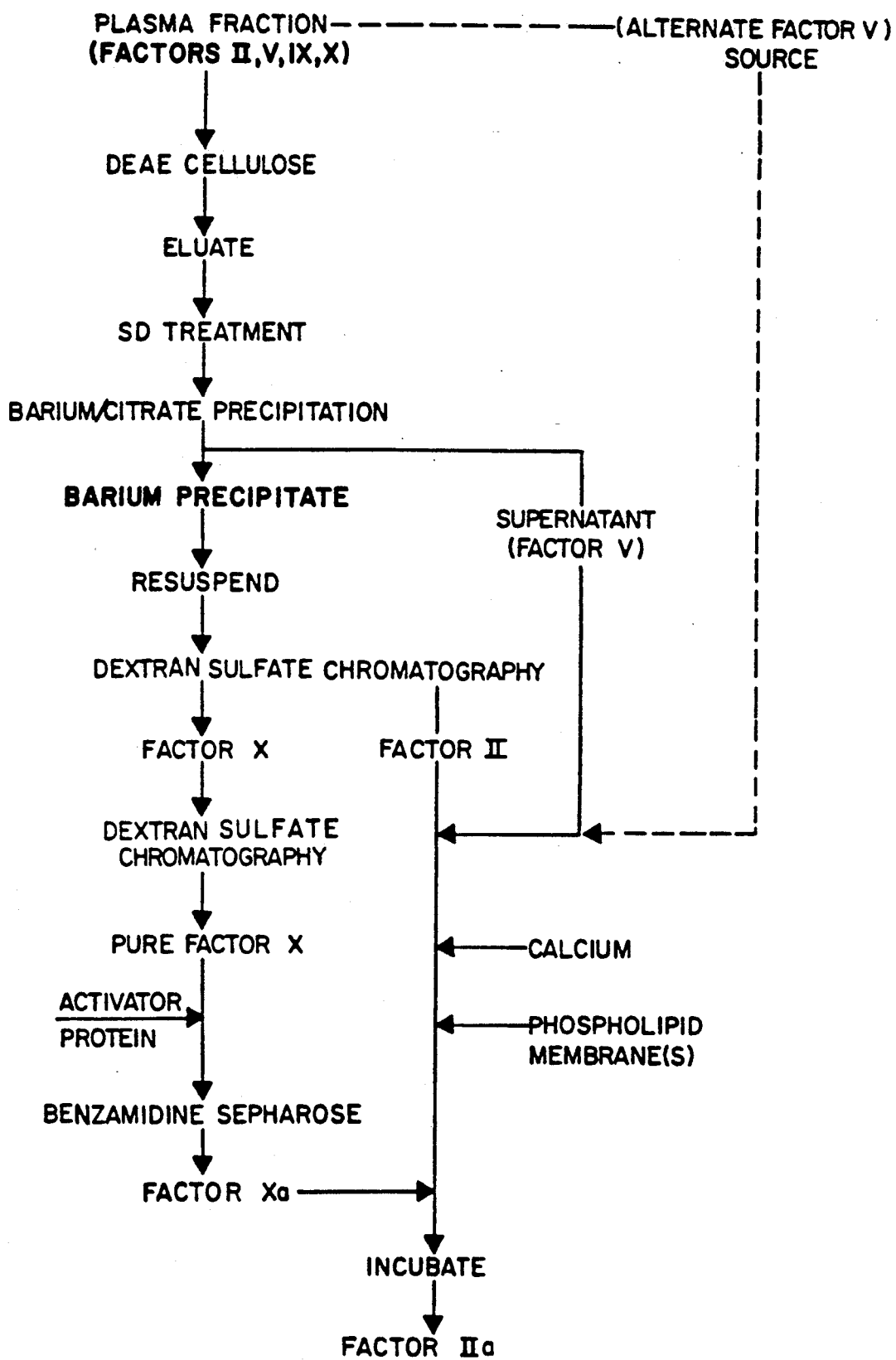

PLASMA FRACTION PURIFICATION

FIELD OF THE INVENTION

This invention relates to a method useful for the preparation of thrombin from purified prothrombin (Factor II) using purified Factor $X_a$, phospholipids, $Ca^{2+}$, and plasma fractions containing Factor $V_a$, where all of the factors (II, $V_a$ and $X_a$) are derived from a single purification procedure.

BACKGROUND OF THE INVENTION

The initiation of blood clotting is by two different, yet similar, molecular mechanisms called the intrinsic and extrinsic coagulation pathways, or cascades. The intrinsic pathway involves factors that are normally in the blood. The extrinsic pathway involves tissue factors in addition to blood components. In each of the reaction steps of the two cascades, a proteinase converts an inactive zymogen into its enzymically active form. In the last step of the cascade, which is the same in both the intrinsic and extrinsic pathways, inactive prothrombin is converted to thrombin, which, in turn, catalyzes the conversion of soluble fibrinogen into insoluble fibrin.

The conversions of zymogens into active proteinases in both cascades are extremely slow in the absence of accessory factors, which stimulate the rates of zymogen activation from $10^4$ to $10^5$ times the rates observed in their absence. Three kinds of accessory factors operate in the cascades: (1) $Ca^{2+}$ ions, (2) acidic phospholipids derived from the membrane bilayers of platelets or damaged tissues, and (3) a protein cofactor that is specifically required for activation of a given zymogen. Prothrombin, which has a molecular weight of about 69,000 to about 80,000, is composed of a single polypeptide chain. Like the activation of all blood coagulation zymogens, activation of prothrombin occurs on a surface provided by negatively-charged phospholipids, such as phosphatidylserine, which are from platelets or damaged tissue. Such lipids are found almost exclusively on the cytoplasmic side, or inside, of the lipid bilayers of cell membranes. Prothrombin does not adhere to erythrocytes or endothelial cells of the vascular system unless the cells are disrupted to expose their inner surfaces. Thus, disruption of cells to expose negatively-charged phospholipids permits prothrombin to bind to the phospholipids. This is a first step in the activation of prothrombin. The binding of prothrombin to the phospholipids is a $Ca^{2+}$-dependent process.

The activation of prothrombin is catalyzed by Factor $X_a$, which also binds to phospholipids through $Ca^{2+}$-dependent interactions. However, maximal rates of activation of prothrombin are obtained only if Factor $V_a$ is also bound to the prothrombin-$X_a$-$Ca^{2+}$-phospholipid complex.

Factor X is a glycoprotein with a molecular weight of about 59,000 to about 70,000 and is composed of two subunits, one subunit having a molecular weight of about 40,000 and the other, about 19,000. Factor X is activated to Factor $X_a$ in both the intrinsic and extrinsic pathways.

Factor V, which has a molecular weight of 330,000, is a glycoprotein composed of one polypeptide chain containing a single, tightly-bound $Ca^{2+}$ that is essential for the activity of $V_a$. Factor $V_a$ is not a proteinase but acts as an accessory protein for prothrombin activation, which acts to increase the rate of prothrombin activation. Factor V itself is activated by thrombin; therefore, in a thrombin activation reaction, generated thrombin activates Factor V to $V_a$, which in turn increases the rate of thrombin synthesis.

Studies in vitro show that $Ca^{2+}$ and phospholipids increase the rate of conversion of prothrombin to thrombin by Factor $X_a$ by about 50 times as compared to the rate of conversion by Factor $X_a$ alone. Factor $V_a$ increases the rate of conversion by $X_a$ about 350-fold, but all factors together increase the rate at least about 20,000-fold. Thus, the $Ca^{2+}$-phospholipid-$X_a$-$V_a$ complex produces the same amount of thrombin in one minute as would be produced by Factor $X_a$ alone in two weeks.

Since thrombin is the active agent in the conversion of fibrinogen to fibrin, the insoluble protein which forms blood clots, thrombin has applications in preventing blood loss from wounds, bleeding ulcers, surgical procedures, and other such injuries. Natural blood clotting requires several minutes to effectively stop the flow of blood from a site of injury; however, the use of thrombin at the site of injury results in immediate clotting. Therefore, topical application of thrombin is desirable in conditions existing after surgery and trauma, or oral application in the treatment of ulcers, to prevent life-threatening, massive blood loss. Also, thrombin infusion into the vitreous cavity during eye surgery can prevent bleeding from sites which are difficult to identify for cauterization. Such treatment reduces the risk of injury to the eye due to an increase in the intraocular pressure during routine surgery.

Currently, bovine thrombin preparations are available for topical applications. However, bovine thrombin preparations often lead to undesirable immunological reactions in patients being treated. Such reactions can be avoided by the use of human thrombin preparations. However, preparations of human thrombin are expensive, thus reducing the desirability of their use. Therefore, there is a need for a cost-effective means of purifying and activating prothrombin to thrombin from human sources.

SUMMARY OF THE INVENTION

The present invention describes a process activating Factor II to Factor $II_a$ using Factor $V_a$ and Factor $X_a$, wherein Factors II, $V_a$ and $X_a$ are all derived from a single impure protein fraction.

The activation process comprises the step of adding Factor II to an activation buffer to provide a Factor II solution. The Factor II is prepared by providing an aqueous solution of the impure protein fraction. Factors II, V and X, contained in the impure protein fraction, are bound to a DEAE ligand and then recovered from the DEAE ligand. The recovered Factor II and X protein fraction is precipitated by the addition of barium chloride. The barium chloride precipitate is dissolved and applied to a chromatographic resin coupled with a ligand which binds Factor X, but which binds Factor II weakly, if at all. Factor II is recovered from the fraction which remains unbound, or only weakly bound, to the Factor X binding ligand.

Factor V is added to the Factor II solution to provide a Factor II/Factor V solution, wherein the Factor V is recovered from the barium chloride supernatant generated by the Factor II preparation procedure from an impure plasma fraction. Factor V is activated during the Factor II activation reaction by Factor $II_a$. In the activation reaction, Factor II is activated very slowly in the absence of Factor $V_a$. However, small amounts of Factor $II_a$ are generated. These small amounts of Factor $II_a$ are then available to activate Factor V to Factor $V_a$, and some Factor $V_a$ is also generated during the purification process. The Factor $V_a$ thus generated is then available to interact in the Factor II activation reaction, which results in an increase in the rate of Factor $II_a$ synthesis. Therefore, no separate activation step for Factor V is required.

Factor $X_a$ is added to the Factor II/Factor V solution to provide a Factor II/Factor V/Factor $X_a$ solution. The Factor $X_a$ is prepared by recovering Factor X from the Factor X binding ligand of the Factor II preparation procedure. The Factor X is activated by specific proteolytic cleavage.

Phospholipid membranes and calcium ions are added to the Factor II/Factor V/Factor $X_a$ solution, and the resultant mixture is incubated to activate the Factor II to Factor $II_a$.

BRIEF DESCRIPTION OF THE DRAWINGS

The features, aspects, and advantages of the present invention will be more fully understood when considered with respect to the following detailed description, appended claims and accompanying drawing which is a flow diagram showing a preferred embodiment of the process of the invention.

DETAILED DESCRIPTION

The process provided in accordance with practice of this invention relates to separation of Factors II, V and X from a single impure protein fraction. As used herein, "impure protein fraction" means a protein fraction which includes one or more protein(s) in addition to Factors II, V and X. Factor X is then activated and added to an activation reaction, which also contains calcium, phospholipids and Factor V, to activate the Factor II zymogen to active, catalytic Factor $II_a$.

Purification of Factors II, V and X

The purification of Factors II, V and X, which is illustrated in the flow diagram, is from human plasma that has been collected and tested according to procedures approved by the U.S. Food and Drug Administration. The plasma may be cryoprecipitated prior to the purification step, if desired. The plasma fraction may be electrodialyzed to reduce the sodium concentration from its original value to between 85 and 105 mM. The dialyzed plasma is then adjusted to about a neutral pH by the addition of acetic acid.

Factors II, V, IX and X contained in the pH-adjusted plasma are adsorbed onto regenerated DEAE (diethyl aminoethyl) cellulose, DEAE sephadex, or other suitable ion-exchange medium, i.e. medium which binds Factors II, V, IX and X, which has been equilibrated with a buffer, such as about 0.03 M sodium phosphate, at a pH of about 6.8, and about 0.03 M sodium citrate (phosphate/citrate buffer). The DEAE resin and cryoprecipitated plasma are mixed for approximately 30 minutes, and the DEAE resin is then collected by centrifugation. The DEAE resin is washed with a buffer such as phosphate/citrate buffer. The wash is discarded.

The washed DEAE resin is suspended in a buffer such as phosphate/citrate buffer. The resulting suspension is then poured into a column, and the eluate is discarded. The DEAE resin is washed with a buffer such as phosphate/citrate buffer, and this wash is also discarded. Factors II, V, IX and X are eluted by washing the DEAE resin with an eluting buffer comprising about 0.03 M sodium phosphate, at a pH of about 6.8, and about 0.03 M sodium citrate, with about 0.2 M NaCl. The eluate is collected, and the Factor II-, V-, IX- and X-containing fractions are pooled and collected in a bulk solution. Appropriate tests of the collected fractions are made and, after the pH of the bulk solution is adjusted to about neutral, the solution is filtered through a sterile bacteria-retentive cartridge or membrane to thereby form a bulk solution of Factors II, V, IX and X. The bulk solution is frozen until processed further.

For further processing, the bulk solution is thawed and may be diafiltered using a "Millipore Pellicon" concentrator, provided by Millipore Corp. of Bedford, Mass., to concentrate the eluate to about 10 g of protein/l. In one exemplary embodiment, the Factors II, V, IX and X containing bulk solution is treated to inactivate any viral contamination contained in the solution. The viral inactivation step (also called the solvent-detergent or SD treatment) is conducted by mixing the diafiltered bulk solution with an aqueous solution comprising about 3% (v/v) Tri-(n)butyl phosphate and about 10% polysorbate 80. About 0.08 to about 0.14 kg of the Tri-(n)butyl phosphate, polysorbate 80 solution are added per kg of bulk solution. The resultant solution is mixed at about 27° C. for about 6 to about 8 hours. The treated Factor II-, V-, IX- and X-containing solution is then processed further in accordance with the process of this invention.

Purification of Factors II, V and X by Barium/Citrate Precipitation

In one exemplary embodiment of the practice of this invention, viral inactivated Factor II-, V-, IX-, and X-containing solution, produced as described above, is diluted approximately 2- to 10-fold with a diluting buffer (0.02 M sodium citrate, at a pH of about 7.3 to about 7.5). If desired, Factor II-, V-,IX- and X-containing solution which has not been viral inactivated, or which has been viral inactivated by methods other than the method described above, can be used.

A volume of 0.5–2 M barium chloride solution sufficient to precipitate Factors II, IX, and X is added to the dilute Factor II-, V-, IX- and X- containing solution. The resultant barium chloride concentration is about 0.1 to about 0.2 M. The precipitate (also called the barium or Ba precipitate) is collected and dissolved in a solution of 0.2 to 0.6 M EDTA ((Ethylene-dinitrilo) tetra acetic acid) and diafiltered, as described previously, against a low-sodium buffer (0 to about 0.2 M NaCl in a solution buffered to a pH between about 6.0 and about 9.0) to remove barium and EDTA and to obtain a desirably-low sodium concentration for further processing. A suitable buffer for the diafiltration comprises about 0.02 M sodium citrate, at a pH of about 6.6 to about 7, and about 0.05 M NaCl.

The supernatant, which contains Factor V, is separately diafiltered, as described previously, against a buffer comprising about 0.06 M Tris, pH 7.2, 0.09 M NaCl, and 0.01 M $CaCl_2$. The Factor V-containing solution is frozen until required for use.

It has been found that barium chloride precipitation yields an increase in the specific activity of Factors II, IX, and X of from about 1.2 to about 3.

The diafiltered, dissolved-barium precipitate is applied to a column containing a silica resin coupled with dextran sulfate (DSS).

Preparation of Dextran Sulfate Silica Resin

In one exemplary embodiment of preparing a DSS resin useful in practice of principles of this invention, activated silica resin, supplied by SERVA Fine Biochemicals Inc. of Westbury, N.Y., under the trademark CNBR SP500, was used as described in U.S. Pat. No. 4,725,673, and incorporated herein by this reference. Briefly, 1 kg of the resin, which is supplied in its CNBr-activated form, was gently slurried with 2 kg of distilled water and then aspirated to dampness in a Buchner funnel. The slurry/wash step was repeated twice more. A dextran sulfate solution was prepared by dissolving 10-200 grams of dextran sulfate in a buffered solution, preferably about 0.1 M $NaHCO_3$ (at a pH of about 8.3), and the washed silica resin and dextran sulfate solutions were combined and mixed for from 1 to about 24 hours to couple the dextran sulfate ligand to the activated silica resin. The ligand-coupled resin was then washed three times with one or more volumes of distilled water in a Buchner funnel and aspirated to dampness. The ligand-coupled resin was then further washed, several times, with a solution containing about 2.0 to about 4.0 M NaCl, at a pH of about 6 to about 8, using a Buchner funnel and aspirated to dampness. The resin was further washed by similar washes and aspirations with one or more volume(s) of a buffered solution, at a pH of about 6 to about 8, containing about 0 to about 0.2 M NaCl.

The washed, ligand-coupled resin was then treated by mixing for from 1 to 10 hours with several volumes of serum albumin to block any "free" binding groups. The blocked, ligand-coupled resin was washed several times with distilled water in a Buchner funnel to remove excess blocking agent. The blocked, ligand-coupled resin was then washed several times with one or more volume(s) of a solution containing about 2.0 to about 4.0 M NaCl, at a pH of about 6 to about 8. A final wash with distilled water was provided, and the resin was aspirated to dampness.

The final preparation step for the ligand-coupled resin included repeated washings with several resin volumes of "alcatone" (a solution of 50% by volume acetone, 35% by volume ethanol, and 15% by volume water). The slurry was stored at 2° C. to 8° C. prior to its use. The resin was decanted from the alcatone and washed with distilled water, at a pH of about 6.8, packed into a column, and equilibrated with between about 0 and about 0.05 M NaCl, at a pH of from about 6 to about 9, prior to use. A suitable buffer for equilibrating the chromatography resin comprises about 0.02 M sodium citrate, at a pH of about 6.6 to about 7, and about 0.05 M NaCl.

Separation of Factor II and Factor X

Usually, between 2 and 5 liters of dextran sulfate silica resin are required for every 5 kg of viral inactivated Factor II, IX and X solution being processed. The dextran sulfate silica resin is preferred, since the silica resin is not easily compressed when used in column chromatography procedures and thus maintains desirable flow rates through such steps. However, other resins, such as sepharose, could be used. Also, while dextran sulfate is specifically described, other ligands, such as heparin, could be used.

A solution containing the diafiltered barium precipitate is prepared as described above. The solution is then pumped through the dextran sulfate silica resin in the column so that Factors IX and X contained in the solution are adsorbed onto the resin. The Factor II remains unabsorbed, or loosely absorbed, and is washed from the column in the breakthrough effluent, or early in the subsequent elution step. After the adsorption step is completed, the Factor IX-, X-adsorbed resin is washed with a volume of wash buffer approximately equal to three times the volume of resin in the column. A suitable wash buffer comprises about 0.02 M sodium citrate, at a pH of about 6.6 to about 7, and about 0.05 M NaCl. The effluent and the wash solutions, with an $A_{280}$ above background (i.e., the $A_{280}$ reading obtained for the buffer eluted from the column during the equilibration process), both of which contain Factor II, are pooled. The Factor II-containing fractions are either immediately further processed or are frozen and held for later processing.

Factors IX and X are eluted from the resin with a linear salt (NaCl) gradient from about 0.05 M to about 0.6 M NaCl in a buffer solution comprising about 0.02 M sodium citrate, at a pH of about 6.6 to about 7. When the NaCl concentration is about 0.2 M, Factor X is eluted from the column. The Factor X-containing fractions are pooled and are either immediately further processed or are frozen and held for later processing. If desired, the Factor X fractions may be reapplied to DSS resin and eluted as described above, for further purification. The Factor X eluates may be filtered prior to further processing or freezing. When the separately-pooled Factor II, IX and X fractions from several runs have been accumulated, the fractions are each processed further.

When the salt gradient reaches a concentration of about 0.25 M to about 0.4 M, both Factors IX and X are eluted. At a concentration above about 0.4 M, Factor IX alone is eluted. The Factor IX-containing fractions are pooled and are either immediately further processed or are frozen and held for later processing.

For further processing, the Factor X-containing fractions are thawed (if frozen) and combined, and the pH is adjusted to about neutral. This combined pool is then diafiltered against an activation buffer such as about 0.02 M HEPES (4-(2-Hydroxyethyl)-1-piperazine-ethanesulfonic acid), at a pH of about 7.4, and about 0.15 M NaCl, to obtain the correct target parameters of Factor X activity and sodium concentration, which are preferably 0.02 M HEPES, pH 7.4, and 0.15 M NaCl.

The Factor X sterile bulk is sampled for Factor X activity. The Factor X can be frozen until required for use.

For further processing, the Factor II-containing fractions are thawed (if frozen) and combined, and the pH is adjusted to about neutral. This combined pool is then ultrafiltered, to concentrate the Factor II, to obtain the correct target parameters of Factor II activity and sodium concentration. The pH is checked and readjusted, if necessary. If desired, other methods of concentrating Factor II, such as ammonium sulfate precipitation followed by diafiltering, or other suitable means known in the art, may be used.

The Factor II is frozen or freeze-dried until required for use.

Activation of Factor X to Factor $X_a$

In blood, Factor X is activated by Factor $IX_a$ in the presence of Factor $VIII_a$, calcium ions and phospholipids in the intrinsic cascade, and by Factor $VII_a$ in the presence of Factor III, phospholipids, and calcium ions in the extrinsic pathway. Activation of Factor X, in the present invention, can be achieved by the action of these blood factors. Alternatively, other proteolytic enzymes, such as Russell's viper venom, can be used.

Preferably, Factor X, purified by the procedure described above, is activated to its active, catalytic form by incubation with snake venom proteinase derived from Russell's viper (*Vipera russelli*) venom.

About 2 g of Factor X is incubated with 0.5-10 mg/ml Russell's viper venom and 0.005 M $CaCl_2$ at 37° C. for 30 min. to convert the Factor X to Factor $X_a$. At the completion of the activation, the snake venom proteinase is removed by column chromatography on benzamidine-sepharose (supplied by Pharmacia of Uppsala, Sweden). The benzamidine-sepharose is equilibrated with an activation buffer, such as 0.02 M HEPES, pH 7.4, and 0.15 M NaCl. The activated Factor X is applied and bound to the benzamidine-sepharose. Unbound materials are washed from the chromatography medium with activation buffer. The Factor $X_a$ is washed from the chromatography medium with about 0.005 M benzamidine in activation buffer. The eluted Factor $X_a$ is collected and diafiltered against 0.02 M Tris HCl, pH 5.5, and 0.15 M NaCl, and may be stabilized by the addition of 0.1% (wt/wt) albumin and 1% (wt/wt) polyethylene glycol or glycerol. The Factor $X_a$ can be stored frozen until required for use.

Activation of Factor II to Factor $II_a$

The activation of Factor II to Factor $II_a$ is accomplished by the action of both Factors $X_a$ and $V_a$ in the presence of phospholipid membranes and calcium.

Phospholipid membranes are synthesized from individual phospholipids or may be provided by phospholipid/fat emulsions, such as those sold under the trade names SOYACAL and FLUOSOL by Alpha Therapeutic Corporation of Los Angeles, Calif. Phospholipid membranes are synthesized from individual phospholipids, such as phosphotidylserine and phosphotidylcholine, by sonication.

Purified Factor V is obtained as described above, or, alternatively, an impure and unfractionated plasma can be used. Factor V is activated during the Factor II activation procedure by Factor $II_a$. In the activation reaction, Factor II is activated very slowly in the absence of Factor $V_a$. However, small amounts of Factor $II_a$ are generated. These small amounts of Factor $II_a$ are available to activate Factor V to Factor $V_a$, and some Factor $V_a$ is also generated during the purification process. The Factor $V_a$ thus generated is then available to interact in the Factor II activation reaction, which results in an increase in the rate of Factor $II_a$ synthesis. Therefore, no separate activation step for Factor V is required.

To activate Factor II, Factor II, obtained as described above, is diluted to about 2 to about 20 $A_{280}$ units in about 0.06 M Tris buffer, at a pH of about 7.3, with about 0.09 M NaCl, about 0.1 µg/ml Factor $X_a$ fraction, about 30 to about 200 µg Factor V fraction, about 5 to about 50 nmole/ml of phospholipids, about 2 to 20 mM $CaCl_2$ (final concentration), about 0.3% Tri(n)butyl phosphate, and about 1% (wt/wt) polysorbate 80 (final concentration) are added. The mixture is incubated at about 24° C. to about 30° C. for about 5 to about 6 hrs. At the completion of the incubation, the pH of the mixture is adjusted to about 6.5, and the solution may be clarified by the addition of about 5% (wt/wt) PEG (final concentration) and centrifugation.

Factor $II_a$ is recovered from the supernatant by chromatography on sulfapropyl-sephadex, supplied by Pharmacia of Uppsala, Sweden, or other suitable chromatography resin. The chromatography medium is equilibrated with a buffer such as about 0.01 M sodium citrate, at a pH of about 6.5. After applying the Factor $II_a$-containing mixture to the chromatography medium, the chromatography medium is washed with about 0.01 M sodium citrate, at a pH of about 6.5, or other suitable buffer. The Factor $II_a$ is eluted from the chromatography medium with a buffer such as about 0.1 M sodium citrate, at a pH of about 6.7. The Factor $II_a$ is filtered and diafiltered to adjust the composition to about 5-10 mM histidine, pH 6.7, about 0.1-0.2% Ca ions, and about 0.1-0.2 M NaCl. The solution is then sterile-filtered using previously-sterilized, bacteria-retentive cartridges or membrane filters, and is freeze-dried.

EXAMPLE 1

Purification of Factors II, V, IX and X

In one example of practice of this invention for the purification of Factors II, V, IX and X, the Factors II, V, IX and X contained in the cryoprecipitated plasma were adsorbed onto DEAE-cellulose which had been previously equilibrated with 0.03 M sodium phosphate and 0.03 M sodium citrate, at a pH of 6.8. The DEAE cellulose and plasma were mixed for approximately 30 min., and the DEAE cellulose collected by centrifugation was washed with 0.03 M sodium phosphate and 0.03 M sodium citrate, at a pH of 6.8. The wash was discarded.

The washed DEAE cellulose was suspended in 0.03 M sodium phosphate and 0.03 M sodium citrate, at a pH of 6.8, and poured into a column. The eluate was discarded. The DEAE cellulose was washed with 0.03 M sodium phosphate and 0.03 M sodium citrate, at a pH of 6.8, and this wash was also discarded. The Factors II, V, IX and X were eluted by washing the DEAE cellulose with 0.03 M sodium phosphate, 0.03 M sodium citrate, at a pH of 6.8, and 0.2 M NaCl. The eluate was collected, and the Factor II-, V-, IX- and X-containing fractions were pooled and collected into a bulk solution. The solution was filtered through a sterile bacteriaretentive cartridge, then lyophilized. The lyophilized powder was virally inactivated by suspension in n-heptane and heating at 60° C. for 20 hours. Heptane was removed by drying.

About 2.04 Kg of dried powder was reconstituted with approximately 64.5 Kg of cold water for injection (CWFI). The reconstituted powder was diluted with 266.6 Kg of 0.02 M sodium citrate, pH 7.4, and 0.25 M NaCl at 4° C., and mixed for 20 min. at 2° C. to 4° C.

About 53.4 Kg of 1.0 M barium chloride solution (4° C.) was added over the course of 2 hours, and the mixture was stirred for one additional hour. The mixture was kept at between 0° C. and 4° C. during the addition of barium chloride and during mixing. After mixing, the solution was centrifuged in a Sharples centrifuge, keeping the flow rate through the centrifuge at between 0.2 and 0.6 per liter per min., and the temperature of the solution at between 0° C. and 4° C. Approximately 10 Kg of barium chloride precipitate was collected in this manner. The supernatant, which contained Factor V, was collected.

The Factor V-containing supernatant was filtered through a Millipore TP cartridge filter to remove any particulate. The solution was passed through a Millipore Pellicon concentrator and was concentrated to between 1/30 and 1/50 of its original volume. The concentrated solution was then diluted 5-fold with a 0.06 M Tris, 0.09 M NaCl, pH 7.2 ("TBS" solution). Upon this dilution, the material was reconcentrated to its volume prior to the TBS dilution. This concentration and TBS dilution step was repeated three more times. The Factor V solution was concentrated one final time, then diluted to 1/10 to 1/30 of its original volume with TBS, at which point the conductivity of the solution was approximately equal to that of the TBS solution.

To the barium chloride precipitate, about 66.7 Kg of a 0.4 M EDTA solution, at 20° C. to 25° C., was added to dissolve the precipitate, and the precipitate was filtered through a Millipore TP cartridge filter to remove particulate. After filtration, the solution was passed through a Millipore Pellicon concentrator and was concentrated to between 1/5 and 1/10 of its original volume. The concentrated solution was then diluted to its original volume, with 0.02 M sodium citrate and 0.05 M NaCl. The concentration and dilution steps were repeated six more times, at which point, the conductivity of the solution was approximately equal to that of the 0.02 M sodium citrate, 0.05 M sodium chloride solution. After the final dilution, the weight of the diafiltered material was 76.4 Kg. The redissolved precipitate contained Factors II, IX, and X.

Half of the diafiltered material (38.6 Kg), containing Factors II, IX, and X, was applied at a flow rate of about 170 ml/min. to a 18 cm x 94 cm Moduline chromatographic column containing dextran sulfate silica resin (DSS), equilibrated with wash buffer (0.02 M sodium citrate and 0.05 M sodium chloride, pH 6.8). The effluent which contained Factor II was collected. Subsequently, 425 Kg of wash buffer was passed through the column.

Approximately 25 liters (1 column volume of wash) of the initial wash was combined with the Factor II effluent. The Factor II pool was concentrated by diafiltration using the Millipore Pellicon concentrator. After concentration, the Factor II eluate was filtered through a (sterile) 0.2 micron filter, then frozen.

Immediately after the column was washed as described above, a 150-liter, linear salt gradient from 0.05 M NaCl to 0.6 M NaCl in 0.02 M sodium citrate, pH 6.8, was applied to the column at a flow rate of 650 ml/min. 3.25 liter aliquots of the column eluent were collected during the gradient, and every third fraction was assayed to determine its Factor IX and X activity. After completion of the gradient, an additional 75 liters of the solution containing 0.02 M sodium citrate, pH 6.8, and 0.5 M NaCl, was applied to the column, and 3.25-liter aliquots of the eluent were collected and assayed for Factor IX and Factor X activity. Those aliquots containing relatively-high Factor X activity, but low Factor IX activity, were pooled to form a Factor X eluate pool. The Factor X eluate pool was concentrated by diafiltration using the Millipore Pellicon concentrator. After concentration, the Factor X eluate was filtered through a (sterile) 0.2-micron filter, and then frozen.

Material from the starting Factor II-, IX- X-containing concentrate and the concentrated Factor II pool were assayed for Factor II activity and protein content. The starting Factor II-, V-, IX- and X-containing concentrate and the concentrated Factor X aliquot pool were assayed for Factor X activity and protein content. The results of these assays are shown in Table I.

TABLE I

|  | Total Units | Yield[2] % | Specific Activity Units/$A_{280}$ |
|---|---|---|---|
| Factor II |  |  |  |
| Plasma fraction | 1.4 × $10^{6*}$ | — | 4.79 |
| DSS Conc.[1] | 8.91 × $10^5$ | 63.6% | 5.38 |
| Factor X |  |  |  |
| Plasma fraction | 6.3 × $10^{5*}$ | — | 2.2 |
| DSS Conc. | 6.67 × $10^4$ | 10.6% | 20.5 |
| Factor V** |  |  |  |
| Plasma fraction | ND | — | 0.017 |
| Ba Supernatant | ND | 46% | 0.027 |

*Estimated from the average Factor II/Factor IX and Factor X/Factor IX ratios derived from 45 separate preparations.
**Factor V results based on separate laboratory experiment using other methods. No data available from preparation described in Example 1.
ND = Not Determined.
[1]Concentrated eluate from the dextran sulfate chromatography step.
[2]% yield is the number of units recovered in the step relative to the number of units in the starting material multiplied by 100.

The purity (specific activity) of Factor II was increased 12% by dextran sulfate chromatography. The purity of Factor V was increased 60% by barium precipitation. The purity of Factor X was increased 10-fold by dextran sulfate chromatography.

EXAMPLE 2

Activation of Factor X to Factor $X_a$

About 460 mg Factor X, prepared in accordance with the procedure of Example 1, was incubated with 1-2 mg Russell's viper venom and 5 mM $CaCl_2$ in a total volume of 1,300 ml at 37° C. for 30 min. to convert the Factor X to Factor $X_a$. At the completion of the activation, the snake venom proteinase was removed by column chromatography on benzamidine-sepharose. The benzamidine-sepharose was equilibrated with 0.02 M HEPES, pH 7.4, 0.15 M NaCl. The activated Factor X was applied and bound to the benzamidine-sepharose. Unbound materials were washed from the chromatography medium with 0.02 M HEPES, pH 7.4, 0.15 M NaCl. The Factor $X_a$ was eluted from the chromatography medium with 0.02 M HEPES, pH 7.4, 0.005 M benzamidine. The eluted Factor $X_a$ was collected, dialyzed against 0.02 M Tris, pH 5.5, 0.15 M NaCl, and stabilized by the addition of 0.1% (wt/wt) albumin and 1.0% (wt/wt) polyethylene glycol.

The activation and purification resulted Factor $X_a$ with a specific activity of about 1,200 units/mg.

EXAMPLE 3

Preparation of Phospholioid Membranes

Seventy-five mg of phosphotidylserine and 225 mg of phosphotidylcholine were mixed and sonicated for 30–45 min. at 4° C. to produce synthetic phospholipid membranes.

EXAMPLE 4

Small Scale Activation of Factor II to Factor $II_a$ 200 mg of Factor II, prepared in accordance with the procedure of Example 1, was diluted to 5 mg/ml in 0.06 M Tris buffer, at a pH of 7.3, containing 0.09 M NaCl, and 4 μg of Factor $X_a$, prepared in accordance with procedure of Example 2; 400 μl of barium chloride supernatant containing Factor V, prepared in accordance with the procedure of Example 1; 10 nmoles/ml of phospholipids, prepared in accordance with the procedure of Example 3; 7 mM CaCl$_2$, 0.3% (wt/wt) Tri-(n)butyl phosphate, and 1% (wt/wt) polysorbate 80 were added. The reaction mixture was incubated at room temperature for 6 hrs.

At the completion of the incubation, the pH of the mixture was adjusted to 6.7, brought to a final concentration of 5% PEG (wt/wt) by the addition of PEG, and mixed at room temperature for 30 min. to dissolve the PEG. The precipitate was removed by centrifugation at 3,000 rpm for 30 min. The resultant PEG supernatant was diluted with an equal volume of distilled water and mixed with 9.2 ml of sulfapropyl-sephadex (which had been equilibrated with 0.01 M sodium citrate, at a pH of 6.5), for 1 hr. at 4° C. The Factor II-containing sulfapropyl-sephadex was then poured into a column and washed with 0.01 M sodium citrate, at a pH of 6.7. The Factor II$_a$ was then eluted with 0.1 M sodium citrate, at a pH of 6.5. Factor II with a specific activity of 1,220 units/A$_{280}$ unit was produced by the small-scale activation procedure, with a yield of 85%. The results are summarized in Table II.

TABLE II

| Step | Total Units ($\times 10^{-6}$) | Yield* % | Specific Activity (units/ A$_{280}$ units) |
|---|---|---|---|
| Incubated Reaction Mixture | 157,000 | 100 | 560 |
| PEG supernatant | 130,000 | 83 | 500 |
| SP-sephadex eluate | 134,000 | 85 | 1,220 |

*% yield is the number of units recovered in the step relative to the number of units in the starting material multiplied by 100.

EXAMPLE 5

Pilot-Scale Activation of Factor II to Factor II$_a$ 20 g of Factor II, prepared in accordance with the procedure of Example 1, was diluted to 5 mg/ml in 0.06 M Tris buffer, at a pH of 7.3, containing 0.09 M NaCl; 0.4 mg of Factor X$_a$, prepared in accordance with the procedure of Example 2; and 100 ml of barium chloride supernatant containing Factor V, prepared in accordance with the procedure of Example 1, were added, and the solution was brought to a final concentration, and 28 nmoles/ml of phospholipids, prepared in accordance with the procedure of Example 3, 7 mM CaCl$_2$, 0.3% (wt/wt) Tri-(n)butyl phosphate, and 1% (wt/wt) polysorbate 80 were added. The activation mixture was incubated at room temperature for 6 hr. At the completion of the incubation, the pH of the mixture was adjusted to 6.5, brought to a final concentration of 5% PEG (wt/wt) by the addition of solid PEG, and mixed at room temperature for 30 min. to dissolve the PEG. The mixture was then centrifuged at 3,000 rpm for 30 min. to remove the PEG precipitate. The resultant supernatant was diluted with an equal volume of distilled water and mixed with one liter of sulfapropyl-sephadex (which had been equilibrated with 0.01 M sodium citrate, at a pH of 6.5) for 1 hr. at 4° C. The Factor II-containing sulfapropylsephadex was then poured into a column and washed with 0.01 M sodium citrate, at a pH of 6.5. The Factor II was then eluted with 0.1 M sodium citrate, at a pH of 6.7. Factor II with a specific activity of 1,100 units/ml was produced by the pilot-scale activation procedure, with a yield of about 75%. The results are summarized in Table III.

TABLE III

| Step | Total Units ($\times 10^{-6}$) | Yield* % | Specific Activity (units/ A$_{280}$ units) |
|---|---|---|---|
| Incubated Activation Mixture | 21 | 100 | 520 |
| PEG supernatant | 17.9 | 85.2 | 480 |
| SP-sephadex eluate | 15.7 | 74.8 | 1,100 |

*% yield is the number of units recovered in the step relative to the number of units in the starting material multiplied by 100.

The above description of exemplary embodiments for purification of Factors II, V, IX, and X and for the activation of Factor X to X$_a$ are for illustrative purposes. Because of variations which will be apparent to those skilled in the art, the present invention is not intended to be limited to the particular embodiments described above. Also, the invention disclosed may be practiced in the absence of any element which is not specifically disclosed in the specification. The scope of the invention is defined by the following claims.

What is claimed is:

1. A process for purifying each of Factor II, Factor V and Factor X from a single impure protein fraction which includes Factors II, V and X, comprising:
   providing an aqueous solution of the impure protein fraction;
   contacting the aqueous solution with a first ligand to thereby bind Factors II, V and X to the first ligand;
   recovering a Factor II, V and X protein fraction from the first ligand;
   adding barium chloride to the recovered Factor II, V and X protein fraction to produce a barium precipitate comprising Factors II and X;
   recovering Factor V from the supernatant of the barium precipitation;
   dissolving the barium precipitate in an aqueous solution to form a Factor II- and X- containing solution;
   applying the Factor II- and X-containing solution to a second ligand capable of binding Factor X but which binds Factor II weakly or not at all;
   binding Factor X to the second ligand;
   recovering Factor II from the fractions which do not bind, or which weakly bind, to the second ligand; and
   recovering Factor X from the second ligand.

2. The process recited in claim 1, wherein the first ligand is a DEAE ligand.

3. The process recited in claim 2, wherein the Factor II, V and X protein fraction is recovered from the DEAE ligand by elution with about 0.2 M NaCl.

4. The process recited in claim 1, wherein the Factor II, V and X protein fraction is precipitated by the addition of barium chloride to a final concentration of about 0.01 M to about 0.22 M.

5. The process recited in claim 1, wherein the second ligand is a dextran sulfate.

6. The process recited in claim 1, wherein the Factor X is recovered from the second ligand by elution with 0.2 M NaCl.

7. A process for separating Factor II from an impure protein fraction which includes Factor II, comprising:

providing an aqueous solution of the impure protein fraction;

contacting the aqueous solution with a first ligand to thereby bind Factors II, V and X to the first ligand;

recovering a Factor II, V and X protein fraction from the first ligand;

adding barium chloride to the recovered Factor II, V and X protein fraction to produce a barium precipitate comprising Factors II and X;

dissolving the barium precipitate in an aqueous solution to form a Factor II- and X- containing solution;

applying the Factor II- and X-containing solution to a second ligand which binds to Factor X but which binds weakly or not at all to Factor II; and recovering Factor II from the fractions which remain unbound, or weakly bound, to the second ligand.

8. The process recited in claim 7, wherein the first ligand is a DEAE ligand.

9. The process recited in claim 8, wherein the Factor II, V and X protein fraction is recovered from the DEAE ligand by elution with about 0.2 M NaCl.

10. The process recited in claim 7, wherein the Factor II, V and X protein fraction is precipitated by the addition of barium chloride to a final concentration of about 0.1 M to about 0.2 M.

11. The process recited in claim 7, wherein the second ligand is a dextran sulfate.

12. A process for separating Factor V from an impure protein fraction which includes Factor V, comprising:

providing an aqueous solution of the impure protein fraction;

contacting the aqueous solution with a first ligand to thereby bind Factors II, V and X to the first ligand;

recovering a Factor II, V and X protein fraction from the first ligand;

adding barium chloride to the recovered Factor II, V and X protein fraction to produce a barium precipitate comprising Factors II and X; and recovering Factor V from the supernatant of the barium precipitation.

13. The process recited in claim 12, wherein the first ligand is a DEAE ligand.

14. The process recited in claim 13, wherein the Factor II, V and X protein fraction is recovered from the DEAE ligand by elution with about 0.2 M NaCl.

15. The process recited in claim 12, wherein the Factor II, V and X protein fraction is precipitated by the addition of barium chloride to a final concentration of about 0.1 M to about 0.2 M.

16. A process for the activation of Factor II to Factor $II_a$ comprising:

diluting Factor II in an activation buffer to provide a Factor II solution, wherein the Factor II is prepared by the process comprising:

providing an aqueous solution of the impure protein fraction comprising Factors II, V and X;

contacting the aqueous solution with a first ligand to bind Factors II, V and X to the first ligand;

recovering a Factor II, V and X protein fraction from the first ligand;

adding barium chloride to the recovered Factor II, V and X protein fraction to provide a barium precipitate comprising Factors II and X;

dissolving the barium precipitate in an aqueous solution to form a Factor II- and X-containing solution;

applying the Factor II- and X-containing solution to a second ligand which binds Factor X but which binds Factor II weakly or not at all; and recovering Factor II from the fractions which remain unbound, or weakly bound, to the Factor X binding second ligand;

adding Factor V to the Factor II solution to provide a Factor II/Factor V solution;

adding Factor $X_a$ to the Factor II/Factor V solution to provide a Factor II/Factor V/Factor $X_a$ solution, wherein the Factor $X_a$ is prepared by:

recovering Factor X from the second ligand of the Factor II preparation procedure; and activating the Factor X by specific proteolytic cleavage;

adding phospholipid membranes and calcium ions to the Factor II/Factor V/Factor $X_a$ solution; and incubating the resultant mixture to activate the Factor II to Factor $II_a$.

17. The process recited in claim 16, wherein the first ligand is a DEAE ligand.

18. The process recited in claim 17, wherein the Factor II, V and X protein fraction is recovered from the DEAE ligand by elution with about 0.2 M NaCl.

19. The process recited in claim 16, wherein the Factor II, V and X protein fraction is precipitated by the addition of barium chloride to a final concentration of about 0.1 M to about 0.2 M.

20. The process recited in claim 16, wherein the second ligand is a dextran sulfate.

21. The process recited in claim 16, wherein the Factor X is recovered from the second ligand by elution with 0.2 M NaCl.

22. The process recited in claim 16, wherein the Factor X is activated by incubation with Russell's viper venom in the presence of calcium ions.

23. The process recited in claim 16, wherein the Factor V is recovered from the barium supernatant generated by the Fraction II preparation procedure.

24. The process recited in claim 16, wherein the Factor V is provided by an aliquot of plasma or cryoprecipitated plasma.

25. The process recited in claim 16, wherein the phospholipid concentration is about 5 to about 50 nmole/ml.

26. The process recited in claim 16, wherein the calcium concentration is about 2 to about 20 mM.

* * * * *

UNITED STATES PATENT AND TRADEMARK OFFICE
CERTIFICATE OF CORRECTION

PATENT NO. : 5,219,995

DATED : June 15, 1993

INVENTOR(S) : S. W. Herring; Y. Uemura; M. Noda; K. T. Shitanishi

It is certified that error appears in the above-identified patent and that said Letters Patent is hereby corrected as shown below:

```
Column 1,   line 39,   before "from platelets" insert
              -- derived --.

Column 6,   line 2,    change "unabsorbed" to -- unadsorbed --.
Column 6,   line 2,    change "absorbed" to -- adsorbed --.

Column 10,  line 17,   change "experiment" to -- experiments --.
Column 10,  line 53,   change "Phospholioid" to
              -- Phospholipid --.

Column 11,  line 19,   change "Factor II" to -- Factor IIa --.
Column 11,  line 66,   change "Factor II" to -- Factor IIa --.
```

Signed and Sealed this

Twelfth Day of April, 1994

Attest:

*Attesting Officer*

BRUCE LEHMAN

*Commissioner of Patents and Trademarks*